United States Patent [19]

Mach

[11] Patent Number: 5,462,860
[45] Date of Patent: Oct. 31, 1995

[54] CONDITIONED CULTURE MEDIUM FOR RAPID GROWTH AND DETECTION OF MICROBES

[75] Inventor: Patrick A. Mach, Shorewood, Minn.

[73] Assignee: Minnesota Mining and Manufacturing Company, St. Paul, Minn.

[21] Appl. No.: 254,750

[22] Filed: Jun. 6, 1994

[51] Int. Cl.[6] .............................. C12M 3/04; C12N 1/00; C12N 1/10; C12N 1/38
[52] U.S. Cl. .................... 435/34; 435/240.1; 435/240.3; 435/240.31; 435/240.54; 435/29; 435/243; 435/287.4; 435/287.9
[58] Field of Search ............................ 435/240.1, 240.3, 435/240.31, 240.54, 29.34, 243, 284, 285, 301

[56] References Cited

U.S. PATENT DOCUMENTS

| | | | |
|---|---|---|---|
| 3,988,314 | 10/1976 | Argoudelis | 536/1 |
| 4,476,224 | 10/1984 | Adler | 435/253 |
| 4,532,206 | 7/1985 | Robinson et al. | 435/36 |
| 4,565,783 | 1/1986 | Hansen et al. | 435/299 |
| 5,089,413 | 2/1992 | Nelson et al. | 435/254 |
| 5,147,801 | 9/1992 | Suzuki et al. | 435/299 |
| 5,232,838 | 4/1993 | Nelson et al. | 435/30 |

FOREIGN PATENT DOCUMENTS 2177419  1/1987  United Kingdom ............ C12Q 1/04

OTHER PUBLICATIONS

Schutte et al. Can J. Microbiol vol. 28 pp. 636–642 (1982).
Enami et al. Gann vol. 74 pp. 845–853 (1983).
Adler et al., "Growth and Division of Filamentous Forms of *Escherichia coli*", *J. of Bacteriology*, vol. 90, No. 1, pp. 223–226, Jul. 1965.
Adler et al., "Repair of Radiation–Induced Damage to the Cell Division Mechanism of *Escherichia coli*", *J. of Bacteriology*, vol. 91, No. 2, pp. 737–742, Feb. 1966.
Adler et al., "A Novel Approach to the Growth of Anaerobic Microorganisms", Biotechnology and Bioengineering Symp. No. 11, pp. 533–540, 1981.
Adler et al., "New Techniques for Growing Anaerobic Bacteria: Experiments with *Clostridium butyricum* and *Clostridium acetobutylicum*", Biotechnology and Bioengineering Symp., No. 13, pp. 153–161, 1983.
Adler et al., "A Technique for Predicting the Solvent–Producing Ability of *Clostridium acetobutylicum*", *Applied and Environmental Microbiology*, vol. 53, No. 10, pp. 2496–2499, Oct. 1987.
Adler, Howard, "The Use of Microbial Membranes to Achieve Anaerobiosis", *Biotechnology*, vol. 10, Issue 2, pp. 119–127, 1990.
Boling et al., "Restoration of Viability to an *Escherichia coli* Mutant Deficient in the 5'→3' Exonuclease of DNA Polymerase I", *J. of Bacteriology*, vol. 160, No. 2, pp. 706–710, Nov. 1984.
Crow et al., "Isolation of Anaerobes Using an Oxygen Reducing Membrane Fraction: Experiments with Acetone Butanol Producing Organisms", *J. of Microbiological Methods*, 4 (1985) 133–139.
Gill et al., "Promotion of Septation in Irradiated *Escherichia coli* by a Cytoplasmic Membrane Preparation", *Radiation Research* 102, pp. 232–240, 1985.

(List continued on next page.)

*Primary Examiner*—Michael G. Wityshyn
*Assistant Examiner*—Jane Williams
*Attorney, Agent, or Firm*—Gary L. Griswold; Walter N. Kirn; Paul W. Busse

[57] ABSTRACT

This invention generally relates to products and processes used to determine the presence of microbes in a sample and particularly relates to a conditioned culture medium which may be used in products and processes to allow early detection and enumeration of such microbes. The conditioned culture medium preferably is a filtered broth made by inoculating viable microbes with gelatin, casein or animal peptones as well as lactose, sodium chloride, bile salts, guar gum and an indicator.

9 Claims, 5 Drawing Sheets

OTHER PUBLICATIONS

Hoskins et al., "Recovery of *Clostridium perfringens* from Food Samples Using an Oxygen–Reducing Membrane Fraction", *J. of Food Protection*, vol. 51, No. 3, pp. 187–191, Mar. 1988.

Phebus et al., "Use of Oxyrase™ Enzyme in Enrichments to Enhance the Recovery of *Escherichia coli* O157:H7 from Culture Media and Ground Beef", *J. of Rapid Methods and Automation in Microbiology* 1, pp. 249–260, 1993.

Yu et al., "Effect of Oxyrase™ Enzyme on *Listeria monocytogenes* and Other Facultative Anaerobes", *J. of Food Safety* 11, pp. 163–175, 1991.

U.S. patent application Ser. No. 08/061,678, Morgan et al., "Method for Rapid Quantification of Microorganism Growth", filed May 14, 1993.

U.S. patent application Ser. No. 08/168,681, Krejcarek et al., "Automated Incubating and Imaging System for a Disposable Microorganism Culturing Device", filed Dec. 17, 1993.

U.S. patent application Ser. No. 08/240,846, Graessle et al,. "Cassette for Disposable Microorganism Culturing Media nad Automated Scanning System", filed May 11, 1994.

CONDITIONED CULTURE MEDIUM FOR RAPID GROWTH AND DETECTION OF MICROBES

This invention generally relates to products and processes used to determine the presence of microorganisms in a sample and particularly relates to a conditioned culture medium which may be used in products and processes to allow rapid growth and detection of coliform bacteria.

BACKGROUND

Classical methods for determining the presence and number of microorganisms in a sample are time consuming, tedious and labor intensive. Typically, a technician must prepare reagents and nutrients, mix the nutrients with agar, heat the mixture, pour the mixture into a petri dish, allow the agar to gel, obtain a test sample, dilute the test sample, add an aliquot of the diluted sample to the agar, incubate the inoculated plate for 24–48 hours and finally count the number of microbial colonies growing in the petri dish. Products and processes which reduce the preparation time and which allow an earlier, more rapid detection and count of these microorganisms, such as bacteria, would clearly be welcomed by those working in this field.

One example of a product which greatly simplifies the above preparation time is a thin film, dry culture device for growing microorganisms that is described in U.S. Pat. No. 4,565,783 to Hansen et al. In a typical thin film device reported by Hansen et al., a cold-water soluble dry powder containing a gelling agent and microbial growth nutrients is coated on a waterproof substrate. A transparent, read-through cover sheet coated on a surface with an acrylate adhesive containing an indicating dye and powdered gelling agent is attached to the coated substrate. A thin film, dry culture plate device based on the report of Hansen et al. for enumerating coliform bacteria in a sample is commercially available as PETRIFILM plates (Catalog No. 6400, 3M, St. Paul, Minn.

When the thin film, dry culture plate device is used, a predetermined amount of an aqueous sample is typically placed in contact with the coated substrate and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of microbial colonies growing on the culture device.

The dry thin film, dry culture plate devices of Hansen et al. are much simpler to use than conventional gelled agar medium/petri dish systems because there is no need for the user to heat and mix the growth medium, agar and other reagents and then add the mixture to petri dishes or pour plates. In addition, the devices of Hansen et al. are compact and easily disposed of and therefore are easier and safer to use. A number of variations and/or modifications of the thin film plates of Hansen et al. have also been reported. For example, Hill et al., U.K. patent application 2 177 419 A, report use of a specific diluent solution to selectively grow lactic acid bacteria on PETRIFILM plates, Nelson et al., U.S. Pat. No. 5,089,413, report a modified thin film device adapted to grow aerobic microorganisms, Suzuki et al., U.S. Pat. No. 5,147,801 report a modified thin film device containing a wet hydrophilic layer or sheet on a water repellant substrate, and Nelson et al., U.S. Pat. No. 5,232,838, report a thin film device incorporating a water-based adhesive to allow use of greater amounts of a sample on the device.

In spite of the many advantages that the thin film, dry culture plates of Hansen et al. and related devices have over conventional types of culture systems, the inoculated thin film plates must still be incubated for 24–48 hours before the number of microbes may be determined. The ability to detect the presence or determine the number of microbes, particular bacteria, at an earlier time may be highly desirable and very valuable in many circumstances.

For example, earlier detection and rapid enumeration of bacteria in a selected sample is important in the food industry. At the present time, the enumeration of bacteria in a sample after an incubation time of 24–48 hours requires processors to delay distribution of food products and may allow the production of large amounts of contaminated food products. Earlier detection of bacteria in food products would allow the processor to release food products for distribution more quickly because contamination or lack of contamination could be established at an earlier time. In addition, a processor might be able locate and correct a source of bacterial contamination without having to discard large amounts of contaminated food products. Thus, detection and enumeration of bacterial contamination in less than 24–48 hours would be extremely beneficial to food product producers. See, e.g., Phebus et al., *Journal of Rapid Methods and Automation in Microbiology*, 1:249–260 (1993) that report use of OXYRASE membrane fraction to shorten the lag phase period of growth of pathogenic *Escherichia Coli* 0157:H7 (a pathogen associated with a 1993 food poisoning outbreak caused by eating undercooked ground beef).

Although the food industry would clearly benefit by determining microbial contamination at an earlier time, other industries would also welcome the opportunity to detect and/or enumerate microorganisms quickly. A need exists for products and processes which allow the early detection and rapid count of microorganisms.

SUMMARY OF THE INVENTION

This invention overcomes the deficiencies of current products and processes referred to above by providing products and processes which allow the early detection and enumeration or rapid count of variety of microorganisms such as gram-positive and gram-negative bacteria and fungi. One embodiment of the present invention is a conditioned culture medium which facilitates the early detection and rapid count or enumeration of such microorganisms growing in the medium. The conditioned medium is a filtered broth that includes gelatin, casein or animal peptones and yeast extract which, before filtering to remove intact microbial cells, is incubated with viable microbes during the microbes log phase period of growth. The conditioned medium also includes sufficient carbohydrates and salts to sustain microbial growth as well as indicators which aid detection of or enumeration of growing microbes.

A particularly preferred conditioned medium contains a filtered broth of 7–14 g of pancreatic digest of gelatin, 6–18 g of yeast extract and 5–10 g of sodium chloride as well as about 20 g lactose, 2.5 g phenol red, 3 g bile salts and 10 g guar gum per one liter of water at a pH of about 7.0.

The culture medium of this invention may be used in broths, in agar or in thin film devices such as PETRIFILM plates. When used in PETRIFILM plates the conditioned culture medium is coated onto a surface of a self-supporting, waterproof substrate and the medium is then dried. When the conditioned medium is used in a dry state on a thin film, the medium preferably contains a filtered broth prepared by first incubating gelatin, casein or animal peptones and yeast extract with viable microbes (during the log growth phase period of the microbes) and then filtering the broth to remove intact cells as well as lactose, other salts, gums or gelling agents and an indicator which allows color changes in the presence of growing microbe and allows visual detection of the microbes. When a preferred dried conditioned medium is rehydrated the above listed components of the culture media are in the same concentrations that are in the preferred liquid culture media described above.

Another embodiment of this invention is a method for detecting the presence of and enumerating microorganisms in a sample. To practice this method, an aliquot of the sample containing microorganisms, such as coliform bacteria, is added to a conditioned medium which is prepared by a process comprising the steps of i) inoculating a broth comprising of gelatin, casein or animal peptones and yeast extract with a microbial culture in which the microbial culture growing in the broth is the same or is different than the microorganisms present in the sample, ii) incubating the broth with inoculating microbes to the log phase of growth, iii) removing the microbes from the broth, and iv) adding carbohydrates and salts to the broth of step iii). Microorganisms which may be present in a sample are then grown in the presence of the conditioned medium and the presence of these microbes may be determined by detecting the color change of an indicator which changes color as the growing microorganisms metabolize nutrients in the medium.

Using this method, the detection and enumeration of microbes in the sample is possible in a range of about 4–14 hours. Detection and enumeration of the microbes growing in the culture medium may be done visually or done using an instrument. A suitable instrument is described in the pending U.S. patent application Ser. No. 08/061,678 filed May 14, 1993, patent application Ser. No. 08/168,681 filed Dec. 17, 1993 and patent application Ser. No. 08/240,846 filed May 11, 1994.

Still another embodiment of this invention is a device to detect microbial growth in a sample. A preferred device includes a self-supporting, waterproof substrate and a transparent cover sheet. The present conditioned medium is coated on the self-supporting, waterproof substrate and then dried. The dried plate is then inoculated with a sample and detection of microbes growing on the device is readily made (either visually or using an instrument) when an added indicator in the device changes color in the presence of selected microbial metabolites in a range of about 4–14 hours.

DETAILED DESCRIPTION

This invention provides products and processes which may be used to rapidly detect and/or enumerate the presence of microbes, such as coliform bacteria, in a sample (coliform bacteria include lactose fermenting, gram-negative rods). Although a variety of products and processes have been used to detect microbes in a sample, a detection and/or enumeration time in a range of about 4–14 hours are significantly shorter than the detection times of conventional products or processes.

Early detection and enumeration or rapid count of microbes in most samples has been problematic for a variety of reasons. In most cases, microbes in samples have been stressed and are not growing at an optimal level. In order to provide for optimal growth (and thus allow early detection) the stressed microbes must be provided a period of time to recover from induced stress. The present invention provides a medium which is believed to afford rapid recovery and accelerate growth of microbes. When used in a thin film culture plate device, a preferred medium includes known reagents and nutrients which are commercially available. These reagents and nutrients include lactose, sodium chloride, digested gelatin and bile salts which are available from Acumedia Manufacturers, Inc., Baltimore, Md. The medium also contains gelling agents such guar gum which is commercially available from Rhone-Poulenc, Inc., Kreuzlinger, Switzerland, indicators such as phenol red which is commercially available from Sigma-Aldrich Corp., Milwaukee, Wis., and triphenyltetrazolium chloride which is commercially available from AMRESCO, Solon, Ohio. The preferred reagents and materials are weighed and mixed in deionized water using conventional aseptic procedures.

The present conditioned culture medium may also include an indicator to aid detection of growing microorganisms. For example a suitable indicator is a pH indicator such as phenol red. Phenol red is a known indicator which changes color from red to yellow in the presence of acid. As a microbial colony grows in a medium containing phenol red, the colony produces metabolic acids which react with the indicator and produce yellow colored areas surrounding the colony. Other known, commercially available indicators may be used in place of phenol red if desired. Alternative indicators include, but are not limited to, colorimetric, fluorescent and ultraviolet substrates as well as enzymatic substrates which are typically capable of reacting to and/or in the presence of growing microorganisms or microbial metabolites. A variety of suitable indicators or probes are listed in Haugland, *Handbook of Fluorescent Probes and Research Chemicals*, 5th ed., 1992 provided by Molecular Probes, Inc., Eugene, Oreg.

Figure 1:
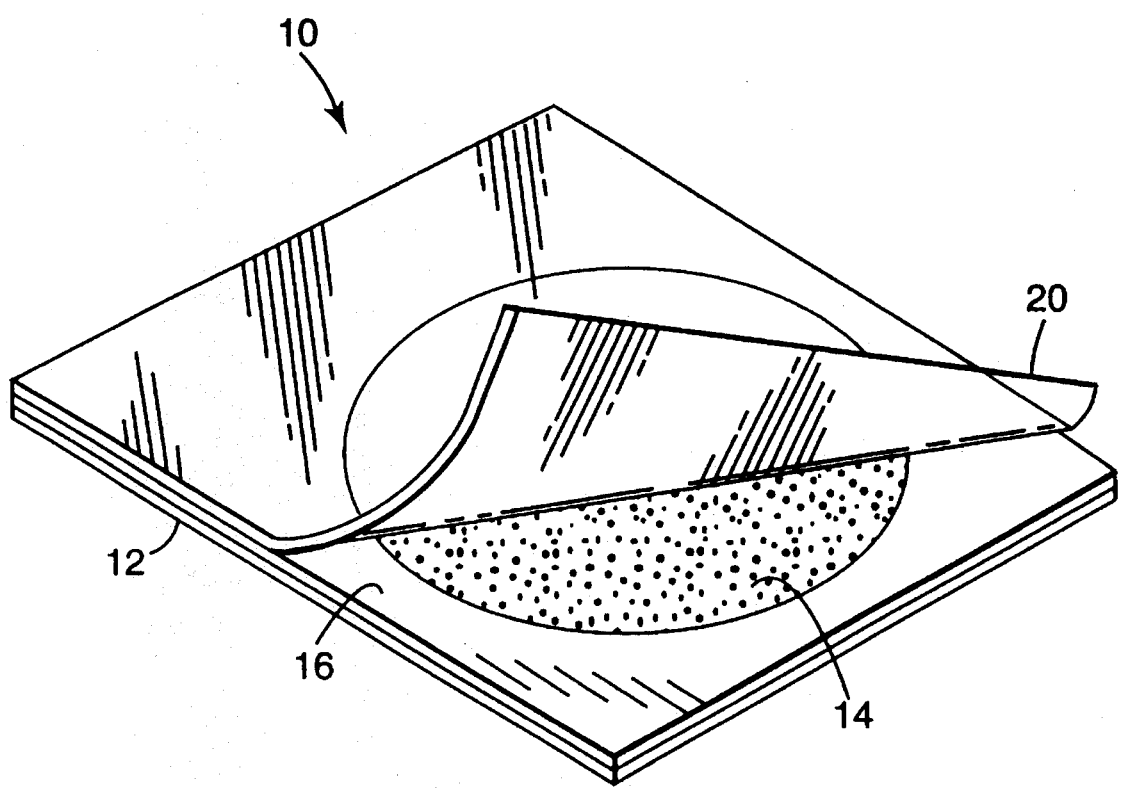
FIG. 1 is an illustration of a device containing conditioned culture medium of the present invention.

FIG. 1 illustrates a thin film culture device suitable for use with the medium of the present invention. Briefly, the device is generally described in U.S. Pat. No. 4,565,783 which is incorporated by reference in this application for the purposes of describing typical processes of making and using these types of culture devices.

The thin film culture device 10 includes a body member having a self-supporting, waterproof substrate 12. Substrate 12 is preferably a relatively stiff material made of a waterproof material that does not absorb water such as polyester, polypropylene, or polystyrene. Other suitable waterproof materials include substrates such as paper containing a waterproof polyethylene coating. The upper surface of substrate 12 is coated with a layer of culture media 14 which is then dried to provide a dry medium 14 on substrate 12. Alternatively, a layer of adhesive may be coated on substrate 12 which serves to hold a culture medium which may be applied as a powder. The adhesive should be sufficiently transparent when hydrated to allow viewing of bacterial colonies growing on the surface of the substrate through the coated substrate. The adhesive should also be coated on the substrate in a thickness which allows the substrate to be uniformly coated with dry culture medium without completely embedding the media in the adhesive.

If the liquid culture medium of this invention is to be used in a dry form or as a dry powder, the reagents, nutrients and indicator are dried. The culture medium of this invention may be readily dried by heating liquid medium in an oven about at 220° F. until essentially all of the water in the liquid has evaporated. If the medium is heated after the water has evaporated, however, the medium begins to degrade.

A foam spacer 16 having a circular opening in the foam is adhered to the medium coated surface of substrate 12. The foam spacer which covers the periphery of substrate 12 defines the area which is to be inoculated with a sample and serves to prevent the sample from leaking from the substrate. In an alternate embodiment, a device may not include a sample-containing foam layer. In this device, the amount of sample is contained on the substrate by the components of the medium alone.

A cover sheet 20 is attached to one edge of an upper surface of the foam spacer 16. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene.

In use, a predetermined amount of inoculum, typically about one milliliter of an aqueous inoculum, is added to the device illustrated in FIG. 1 by pulling back cover sheet 20 and adding an aqueous test sample or water to the middle of substrate 12. Cover sheet 20 is then replaced over substrate 12 and the inoculum is evenly spread on the substrate. A convenient tool to do this is a weighted circular template which also is used to confine the inoculum to a specific area of substrate 12. As the inoculum contacts and is spread on substrate 12, the culture medium on substrate 12 hydrates to form a growth-supporting nutrient gel. The inoculated device is then incubated for a predetermined time after which the number of bacterial colonies growing on the substrate may be counted through the transparent cover sheet 20.

Although the use of the conditioned culture medium of this invention on a thin film device is described above, those of ordinary skill in the art will recognize that the conditioned medium may be used in other culturing devices which are known in the art. For example, the conditioned medium may be used as a broth and used to grow microbes in suspension or the conditioned medium may be use to grow bacteria on known agar plates.

The following examples are intended to provide further details and embodiments related to the practice of the present invention. These examples are provided for illustrative purposes and should not be construed to limit the scope of the present invention which is defined in the appended claims.

Example 1

Preparation and Growth of Bacteria in a Conditioned Culture Medium

This example describes the modification of media components to facilitate more rapid growth of microorganisms and, thereby, facilitating their earlier detection.

To make a conditioned medium, a broth was prepared by adding the following components to two liters of deionized water, adjusting the pH to about 7.0 and sterilizing the resulting mixture at about 250° C. for 15 minutes.

28 g of pancreatic digest of gelatin (Acumedia)

12 g of yeast extract (Acumedia)

20 g of sodium chloride

A culture of *E. coli* 149, ATCC accession number 55535 (1 ml of inoculum cultured in trypticase soy broth) was added as a stationery culture to the above described broth. The resulting culture was incubated at 35° C. for several hours while monitoring growth by absorbance at 620 nm.

At either times 0, 2, 4, 5 and 8 hours (FIGS. 2–4) or times 0 and 2 hours (FIGS. 5–8), 400 ml aliquots of the broth were removed and the removed aliquots were filter sterilized by vacuum filtration (to 0.2 um). To this filtered broth was added the following additional components and the pH of the mixture was adjusted to 7.0 to give a conditioned medium:

8 g lactose (FIGS. 2–4, Acumedia) or 8 g glucose (FIGS. 5–8, Sigma-Aldrich)

1.0 g phenol red (Sigma-Aldrich)

1.2 g bile salts (Acumedia)

4 g guar gum (Rhone-Poulenc)

Thin film dry culture plates were prepared from either the lactose-containing or glucose-containing conditioned medium as follows. The conditioned medium was coated onto a polyester substrate and dried at about 220° F. A thin styrofoam dam was overlaid onto the dried broth to serve as a well on the polyester substrate. The polyester substrate/styrofoam dam was then covered with a polypropylene sheet that had been previously coated on one surface with an copolymeric isooctyl acrylate/acrylic acid adhesive (a copolymer of 98 wt. % isooctyl acrylate and 2 wt. % acrylic acid comonomer) containing ca. 150 mg triphenyl tetrazolium chloride (AMERESCO) and then powder coated over the adhesive with additional guar gum.

Figure 2:
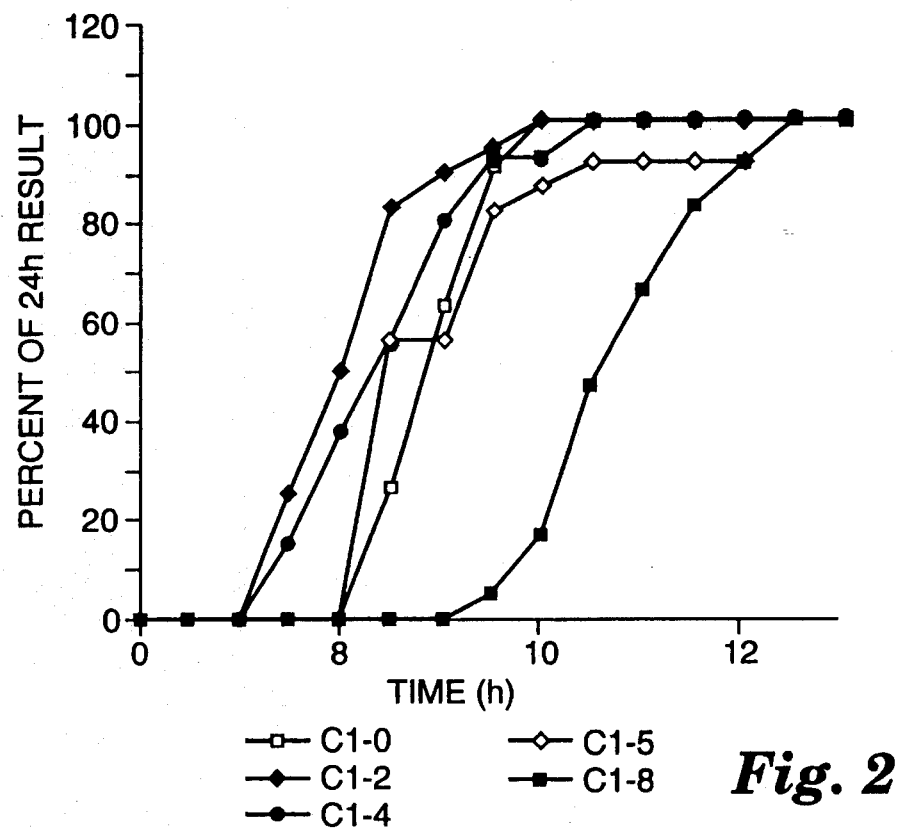
FIGS. 2–8 illustrate the improvement in read-out times, as a percentage of the read-out at twenty-four hours, of different bacteria growing in a conditioned culture medium.
Figure 3:
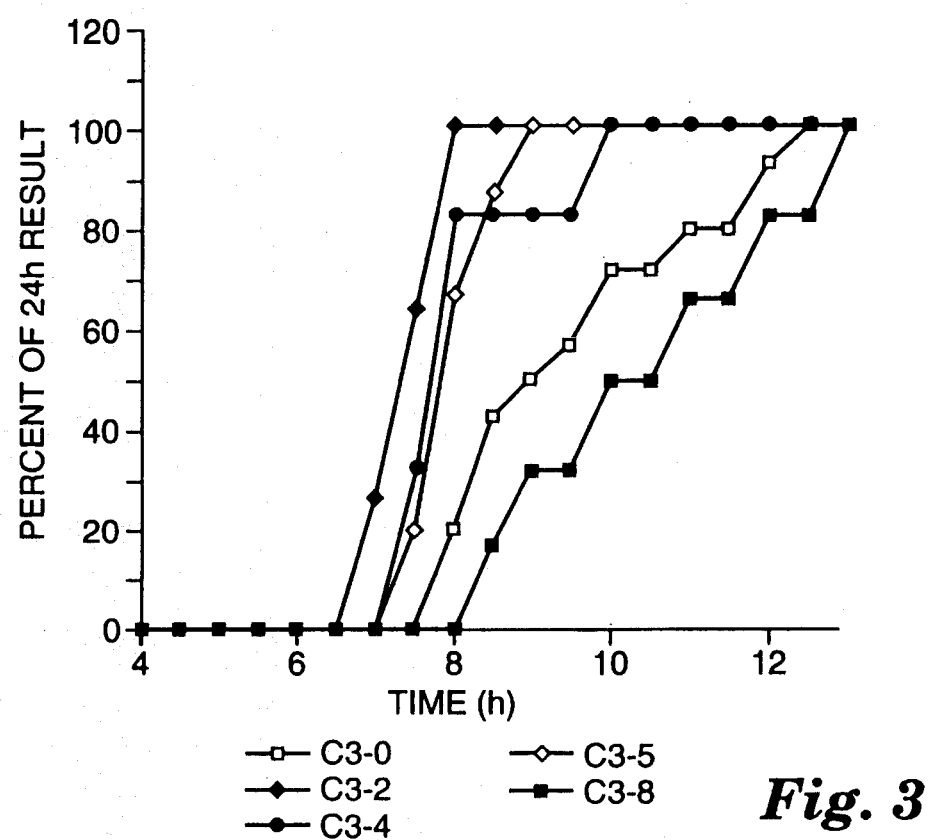
Figure 4:
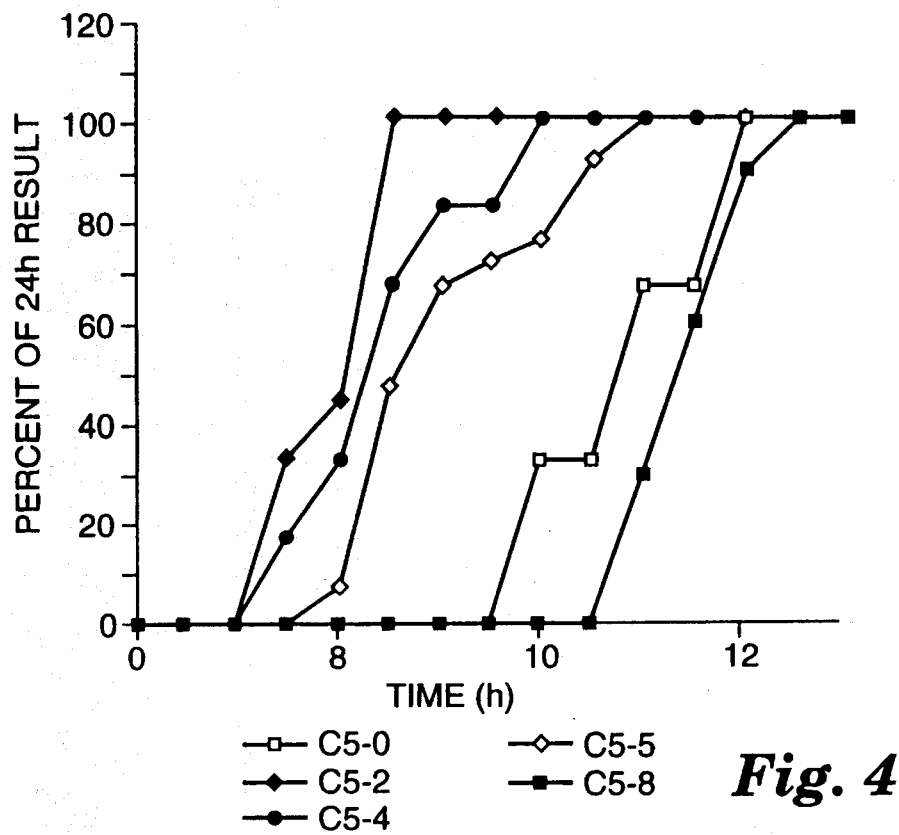
Figure 5:
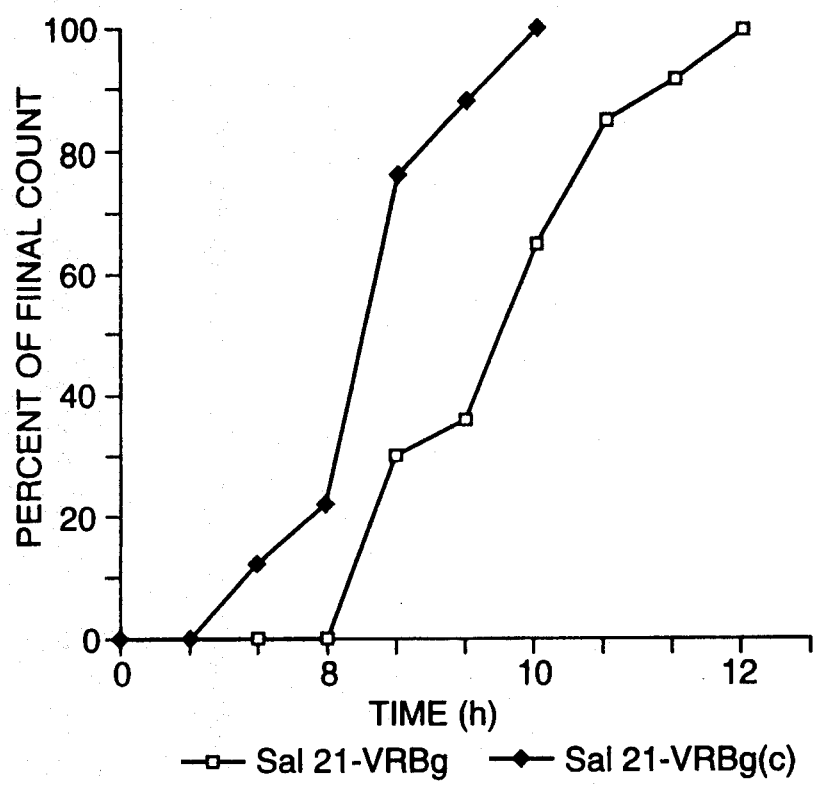
Figure 6:
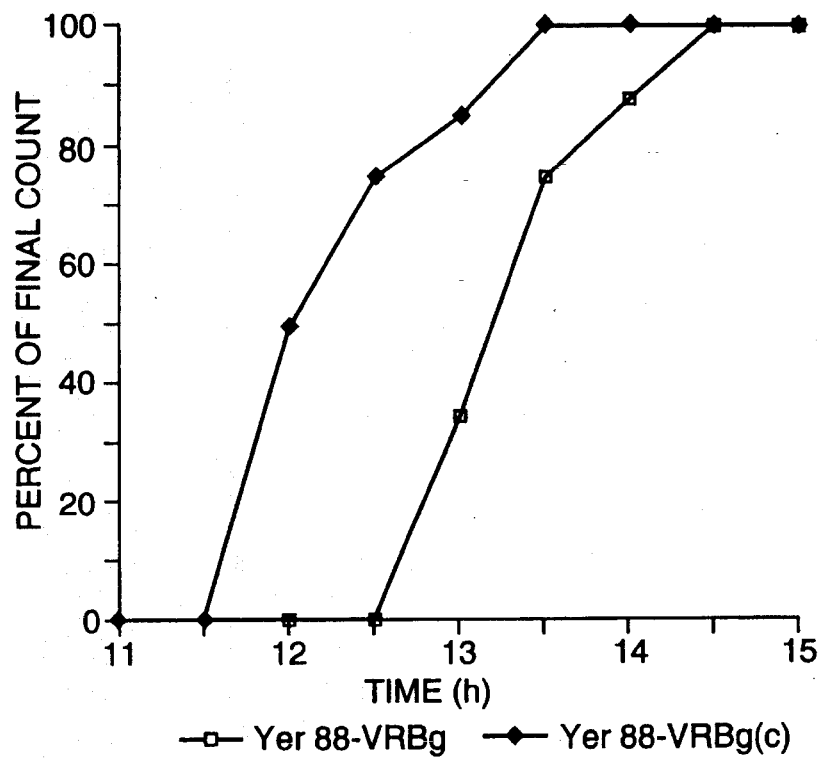
Figure 7:
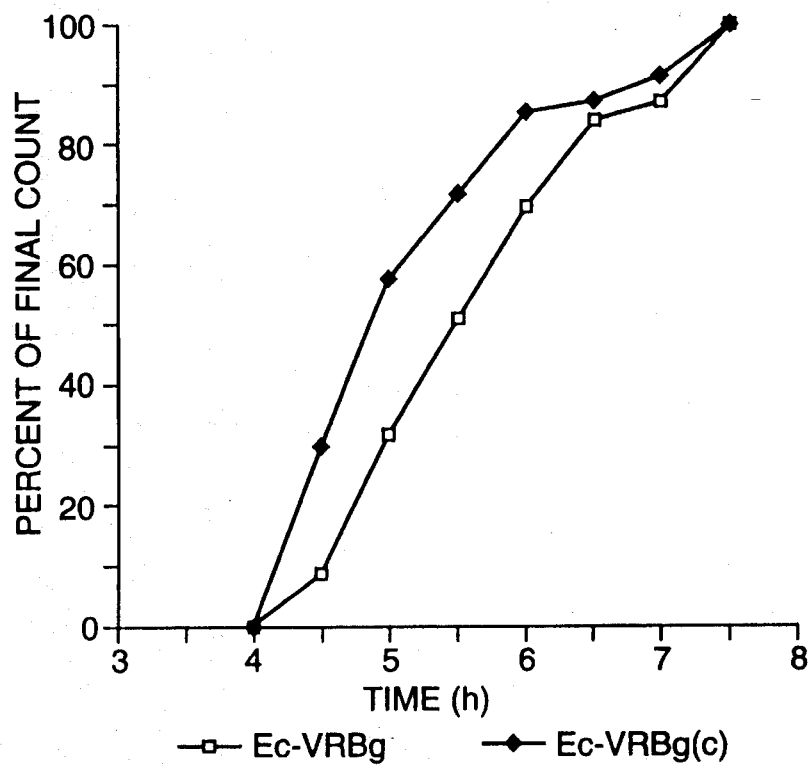
Figure 8:
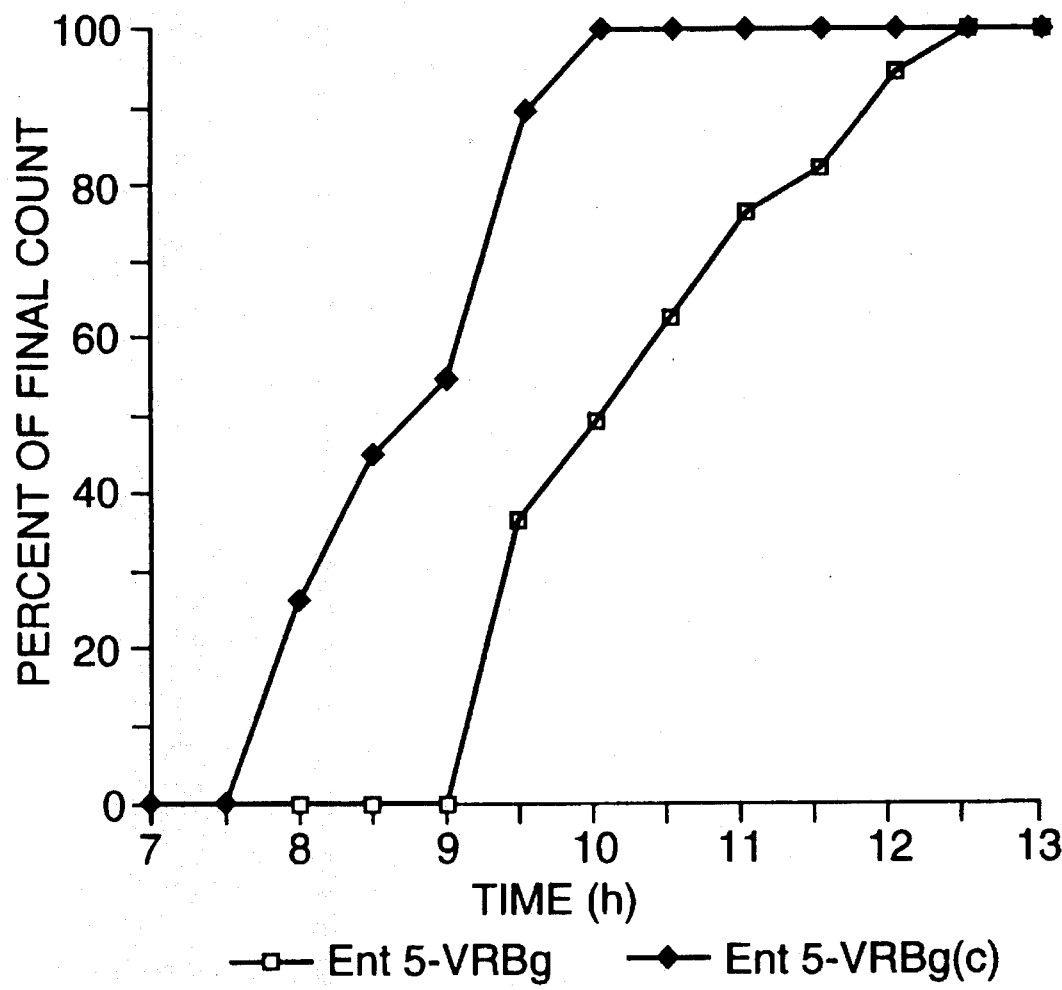

Various bacteria for testing (FIG. 2—*Serratia liquefaciens*, FIG. 3—*Enterobacter sakazaki*, FIG. 4—*Enterobacter cloacae*, FIG. 5—Salmonella sp., FIG. 6—Yersinia sp., all strains were maintained as frozen suspensions at 3M, St. Paul, Minn.) were grown in trypticase soy broth, overnight at 35° C. and then diluted approximately one-hundred million-fold ($10^{-8}$) in a phosphate-buffered saline solution before being added to the thin film plates. The thin film plates were then inoculated (one ml), incubated and examined for growth zones (over time) attributed to acid formation by the growing bacteria. The observed yellow colored growth zones were correlated to the results seen on the control thin film plates at 24 hour and expressed as percentage of the 24 hour result (FIGS. 2–8).

These data graphed on FIGS. 2–8 indicate that compared to controls (broth aliquots taken at time 0 and then made into a thin film culture plate medium by adding lactose, glucose, phenol red, bile salt and guar gum), 1–2 hour earlier detection is possible using conditioned medium and up to 4 hours faster detection and enumeration of the final bacterial colony count is possible using conditioned medium. The data graphed on FIGS. 2–4 also suggests that the optimal initial conditioning time of the broth is between about 2 and 5 hours. Initial conditioning in excess of about 8 hours is consistently observed to provide slower detection and enumeration times compared to controls.

I claim:

1. A conditioned culture medium which facilitates early detection and enumeration of microorganisms selected from the group consisting of Gram positive and Gram negative bacteria and fungi present in a sample, wherein the conditioned medium is prepared by a process comprising the steps of i) inoculating a broth comprising gelatin, casein or animal peptones and yeast extract with a microbial culture wherein the microbial culture is selected from the group consisting of Gram positive and Gram negative bacteria and fungi ii) incubating the broth while the microbial culture is in the log phase of growth, iii) removing the incubated microbial culture from the broth, and iv) adding carbohydrates and salts to the broth of step iii) to give a conditioned medium.

2. The conditioned culture medium of claim 1 wherein the conditioned culture medium of step iv) is dehydrated to give a dry, rehydratable powder.

3. A conditioned medium which facilitates early detection and enumeration of a first microbial culture present in a sample comprising i) a filtered broth comprising gelatin, casein or animal peptones and yeast extract which has been incubated with a second microbial culture in the log phase of growth thereof for a period of time sufficient to allow the second microbial culture grow, wherein the first and second microbial cultures are the same or are different microbial cultures selected from the group consisting of Gram positive and Gram negative bacterial and fungi, and ii) sufficient carbohydrates and salts to allow growth of the first microbial culture in the conditioned medium.

4. The conditioned medium of claim 3 wherein the first and second microbial cultures are coliform bacteria.

5. The conditioned medium of claim 3 wherein the second microbial culture is selected from the group consisting of *Escherichia coli, Serratia liquefaciens, Enterobacter sakazaki, Enterobacter cloacae*, Salmonella sp., and Yersinia sp.

6. A device to detect and enumerate microbial growth in a sample comprising a self-supporting, waterproof substrate, the conditioned culture medium of claim 3 coated on the self-supporting, waterproof substrate and a transparent cover sheet overlaying the culture medium coating.

7. The device of claim 6 wherein the culture medium further comprises an indicator which reacts in the presence of growing microbes and allows visual detection of the growing microbes.

8. A conditioned culture medium which facilitates early detection and enumeration of microorganisms selected from the group consisting of Gram positive and Gram negative microorganisms and fungi present in a sample, wherein the conditioned medium is prepared by a process comprising the steps of i) inoculating a broth comprising digested gelatin, casein or animal peptones and yeast extract with a microbial culture selected from the group consisting of Gram positive and Gram negative microorganisms and fungi, ii) incubating the broth while the microbial culture is are in the log phase of growth, iii) removing the microbial culture from the broth, and iv) adding carbohydrates and salts to the broth of step iii) to give a conditioned medium.

9. A conditioned medium which facilitates early detection and enumeration of a first microbial culture present in a sample comprising i) a filtered broth comprising digested gelatin, casein or animal peptones and yeast extract which has been incubated with a second microbial culture in the log phase of growth for a period of time sufficient to allow the second microbial culture grow, wherein the first and second microbial culture are the same or are different microbial cultures selected from the group consisting of Gram positive and Gram negative microorganisms and fungi, and ii) sufficient carbohydrates and salts to allow growth of the first microbial culture in the conditioned medium.

* * * * *